US00PP14743P2

(12) United States Plant Patent
Speichert et al.

(10) Patent No.: US PP14,743 P2
(45) Date of Patent: May 4, 2004

(54) MISCANTHUS PLANT NAMED 'GILDED TOWER'

(50) Latin Name: *Miscanthus*
Varietal Denomination: Gilded Tower

(76) Inventors: C. Greg Speichert, P.O. Box 154, St. John, IN (US) 46373; Roger Grounds, Apple Ct., Hordle lane, Hordle, Lymingtom, Hampshire SO41 OHU (GB)

( * ) Notice: Subject to any disclaimer, the term of this patent is extended or adjusted under 35 U.S.C. 154(b) by 0 days.

(21) Appl. No.: 10/348,581

(22) Filed: Jan. 21, 2003

(51) Int. Cl.[7] ..... A01H 5/00
(52) U.S. Cl. ..... Plt./384
(58) Field of Search ..... Plt./384

*Primary Examiner*—Bruce R. Campell
*Assistant Examiner*—Annette Para
(74) *Attorney, Agent, or Firm*—Penny J. Aguirre

(57) ABSTRACT

Miscanthus 'Gilded Tower', a sport of Miscanthus 'Giganteus', is a new and unique cultivar that is characterized by its variegated foliage of yellow-green and deep green stripes with a white mid-rib.

2 Drawing Sheets

BACKGROUND OF THE INVENTION

The present invention relates to a new and distinct cultivar of hybrid Miscanthus and will be referred to hereafter by its cultivar name, 'Gilded Tower'. 'Gilded Tower' represents a new cultivar of Giant Miscanthus, an ornamental grass grown for landscape use.

The inventors discovered and selected the new cultivar, 'Gilded Tower', in a cultivated garden in Lymington, Hampshire, United Kingdom in the fall of 1998. 'Gilded Tower' was discovered as a naturally occurring culm sport of the cultivar Miscanthus 'Giganteus' (unpatented), a cultivar of hybrid origin.

The new cultivar 'Gilded Tower' was selected for its unique leaf variegation pattern and is unlike any other known cultivars of Miscanthus known to the inventors. 'Gilded Tower' has leaf variegation that is comprised of longitudinal yellow-green and deep green stripes that vary in width and a white mid-rib. Although the stripe width for each component color is variable, the coloration is present on all foliage and perpetuated through propagation.

The parent plant, Miscanthus 'Giganteus' has deep green foliage with a white mid-rib with no presence of yellow green variegation.

Asexual reproduction of the new cultivar was first accomplished by culm division in Lymington, Hampshire, United Kingdom in the fall of 1998 by the inventors. The characteristics of this cultivar have been determined to be stable and are reproduced true to type in successive generations.

SUMMARY OF THE INVENTION

The following traits have been repeatedly observed and represent the characteristics of the new cultivar. The new Miscanthus has not been observed under all possible environmental conditions. The phenotype may vary somewhat with variations in temperature, day-length, light intensity, soil types, and water and fertility levels without, however, any variance in genotype. The measurements, observations, and descriptions that follow describe plants grown outdoors for two years from a single culm division in St. John, Ind. These attributes in combination distinguish 'Gilded Tower' from any selections of Miscanthus known to the inventors.

1. The foliage of 'Gilded Tower' is variegated with stripes of yellow-green and deep green with a while mid-rib. In the fall the variegation changes to shades of greyed-orange with areas of greyed purple and finally to an overall color that is a light greyed-orange.
2. The flowers of the new Miscanthus arise in late fall and are composed of arching, terminal panicles of slender, silky racemes that open a creamy white color with a purple-red tint and appear silvery as they mature.
3. The plant habit of 'Gilded Tower' is upright with robust, pendant foliage. It is clump-forming and herbaceous, with persistence of leaf and flower panicles throughout the winter. There is some loss of lower leaves during the growing season.
4. 'Gilded Tower' is best grown in moisture-retentive soils in full sun but is tolerant to a wider range of growing conditions and tolerant of wind and partial shade.

BRIEF DESCRIPTION OF THE DRAWING

The photographs used in these drawings were taken of a 2 year old plant grown from a single culm division of 'Gilded Tower' and grown outdoors in a trial bed in St. John, Ind.

The photograph on Sheet One shows the plant habit of 'Gilded Tower' when in bloom.

The two photographs on Sheet Two give a representation of the foliage variegation. The colors in the photographs are as close as possible with conventional photography.

BOTANICAL DESCRIPTION OF THE PLANT

The following is a detailed description of the new cultivar as grown in an outdoor trial bed for two years in St. John, Ind. The color determination is in accordance with the 1995 R.H.S. Colour Chart of The Royal Horticultural Society, London, England, except where general color terms of ordinary dictionary significance are used.

Botanical classification: 'Gilded Tower' is a cultivar of Miscanthus of hybrid origin.

Commercial classification: 'Gilded Tower' Giant Miscanthus.

Parentage: Culm sport of Miscanthus 'Giganteus', a cultivar of Miscanthus of hybrid origin.

General description:

*Blooming period.*—Blooms in late fall or not at all in short growing seasons. Blooms are retained over the winter.

*Plant habit.*—Herbaceous, clump-forming, ornamental grass with an upright form and pendant, robust foliage.

*Height and spread.*—2 to 3 m in height bloom with a spread of 40 to 50 cm in a single growing season from a 3 culm division. Moderate vigor.

*Hardiness.*—Zone 4 to 9.

*Culture.*—Grows best in fertile, moist soil in full sun. Tolerant to wind and partial shade; however, lodging will occur if grown in too much shade.

*Diseases and pests.*—No susceptibility or resistance to diseases or pests that affect Miscanthus has been observed.

*Root description.*—Fibrous, well-banched, very dense root system. Slightly rhizomatous, with shoots arising from 5 to 10 cm from the base of the culms.

Growth and propagation:

*Propagation.*—Culm division, best divided in spring when in active growth.

*Time required for root development from a single division.*—A 3 culm division planted in a bark-based media will fully develop roots in a 5 gallon container in 3 to 4 month, grown outdoors under standard summer temperatures and natural lighting.

Culm (stem) description:

*General.*—Cylindrical, pithy, reed-like, erect, sheathed.

*Culm color.*—Ranges from 144D to 144B with occasional markings on the sheath edges of 59C.

*Culm size.*—0.7 to 1.0 cm in diameter, 2 to 3 m in height from base to tip of flower panicle.

*Stem surface.*—Glabrous.

*Internode length.*—6 to 18 cm.

*Ligule.*—Membranous area, 1 mm in height and 200B in color with very fine white hairs, 1 to 2 mm in length.

Foliage description:

*Leaf shape.*—Linear, widest at base through the midpoint then narrowing to a point at apex.

*Leaf division.*—Simple.

*Leaf base.*—Sheathed.

*Leaf apex.*—Acute.

*Leaf aspect.*—Pendant, leaves are flat to slightly involute.

*Leaf venation.*—Parallel, the midrib is distinct and recessed on the upper surface, mid-rib color is 155D on upper surface only.

*Leaf margins.*—Entire.

*Leaf persistence.*—Some loss of lower leaves during the growing season, those that remain are persistent through winter.

*Leaf attachment.*—Sheathed. Leaf is sheathed from the base of culm and the blade extends out from the culm at a node. Sheath margins are overlapping with a gradually opening at 4 to 5 cm below the node.

*Leaf size.*—2 to 2.5 cm at base, 2 to 3 cm at mid-point, then tapering to a point at the apex. 24 to 36 cm in length.

*Leaf number.*—12 to 18.

*Leaf arrangement.*—Alternate.

*Leaf surface.*—Glabrous on upper and lower surface.

*Leaf color.*—Upper and lower leaves exhibit the same coloration, with the exception of the white mid-rib, which is present on the upper surface only.

Flower description:

*General description.*—Compact panicle, composed of numerous, slender, pubescent racemes, cascading to one side, spikelets arranged in two equal pairs, 2 flowers per spikelet. Upper flower is hermaphrodite, lower flower is sterile.

*Lastingness of inflorescence.*—Panicles are persistent from fall through winter.

*Fragrance.*—None.

*Panicle size.*—Approximately 30 cm in length and 12 cm in width.

*Panicle color.*—Emerges creamy white (effectively 158A) tinted with purple-red (187C) and changes to a silvery color during plant dormancy (effectively 202D).

*Rachis size.*—13 to 18 cm in length, continuous with culm.

*Rachis number.*—Approximately 50.

*Rachis color.*—161B.

*Spikelet bud.*—Emerge with spiklet surrounded by closed glumes, 4 mm in length and 1 mm in width with fine white hairs up to 1 cm in length.

*Spikelet size.*—5 mm in length and 2 mm in width (excluding hairs).

*Spikelet hairs.*—Emerging from the base as a ring, long (up to 1.2 cm in length, very fine.

*Spikelet pedicel.*—Unequal in length in the pairs, 1 mm and 3 mm, 161 in color.

*Glumes.*—2, 164 in color, equal in size, 4 mm in length and 1 mm in width, lanceolate in shape, awn-less.

*Lemmas.*—Lower, sterile flower, papery and translucent 4 mm in length and 0.5 mm in width. No lemma observed for upper fertile flower.

Reproductive organs:

*Androecium.*—Anthers; 2.5 mm in length, 0.75 mm in width, color is 187C changing to 187A, basofixed on very short filament (0.5 mm). Pollen is moderate in quality, 165D in color, longitudinally dehiscence.

*Gynoecium.*—Pistil; 1, 2 plumose stigmas, 1.5 mm in length, 0.5 mm in width, color is 187C changing to 187A. Ovary; 1-locular, superior, minute, not easily quantifiable in size and color.

*Caryopsis.*—None observed.

What is claimed is:

1. A new and distinct cultivar of Miscanthus plant named 'Gilded Tower' substantially as herein illustrated and described.

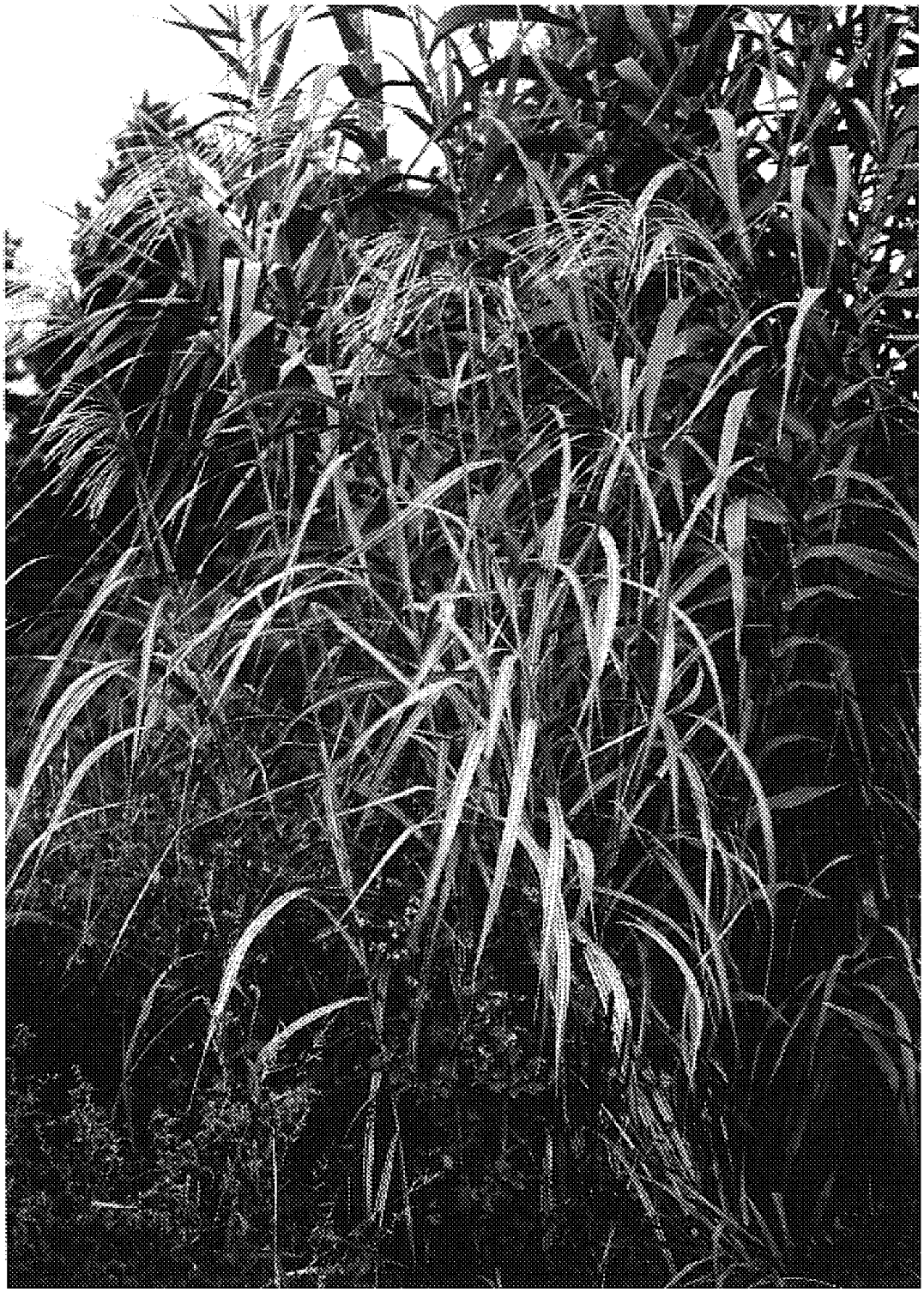

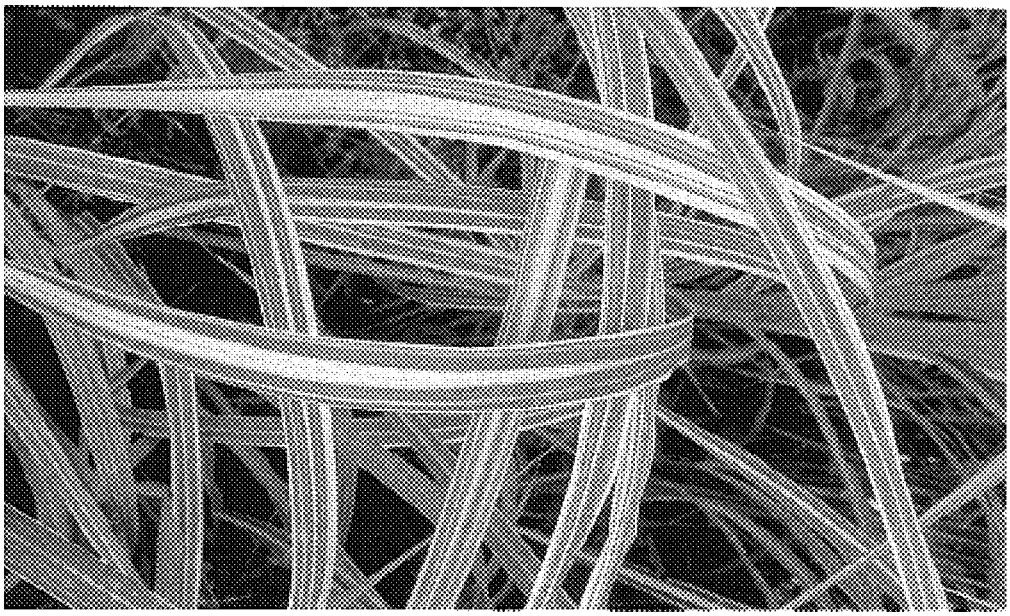
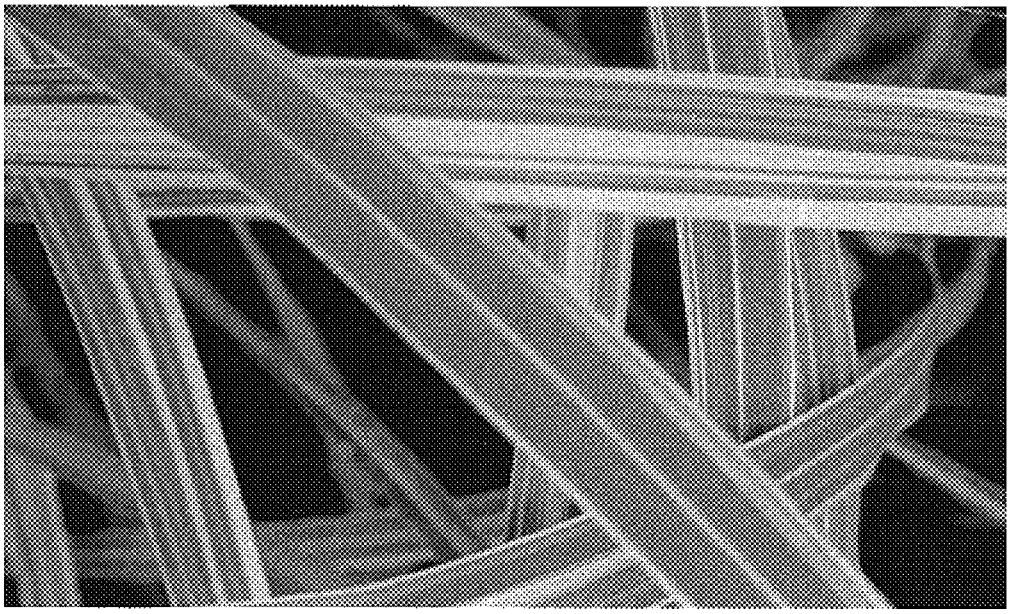

* * * * *